United States Patent [19]

Cooke

[11] Patent Number: 5,498,242
[45] Date of Patent: Mar. 12, 1996

[54] MEDICAL NEEDLE SHEATH AND STAND FOR ONE-HANDED USE

[76] Inventor: Thomas H. Cooke, 651 Strander Blvd. No. 100, Seattle, Wash. 98188

[21] Appl. No.: 427,670

[22] Filed: Apr. 24, 1995

[51] Int. Cl.⁶ .................................................. A61M 5/32
[52] U.S. Cl. .......................... 604/192; 604/263; 128/919; 206/365
[58] Field of Search ................... 604/263, 187, 604/192; 128/919; 206/365, 366

[56] References Cited

U.S. PATENT DOCUMENTS

| | | |
|---|---|---|
| 4,921,199 | 5/1990 | Villaveces . |
| 4,981,476 | 1/1991 | Aichimayr et al. . |
| 5,102,083 | 4/1992 | Baskas . |
| 5,160,324 | 11/1992 | Halbach . |
| 5,183,469 | 2/1993 | Capaccio . |
| 5,242,421 | 9/1993 | Chan .................................. 604/192 X |
| 5,279,577 | 1/1994 | Collett ................................. 604/263 X |
| 5,279,578 | 1/1994 | Cooke ..................................... 604/192 |
| 5,334,173 | 8/1994 | Armstrong, Jr. . |

Primary Examiner—John D. Yasko
Attorney, Agent, or Firm—Graybeal Jackson Haley & Johnson

[57] ABSTRACT

A sheath and stand for one-handed use by a health care user of a medical needle such as a hypodermic needle or a medical electrode, wherein the stand is configured with an aperture or socket for receiving the distal end or tip of the sheath and with hook means at the proximate end of the stand which is engageable with the lip of a collar at the proximate end of the sheath to firmly retain the sheath on the stand. The sheath is readily removable from the stand after a used medical needle is reinserted in the sheath by slight axial withdrawal of the sheath to disengage its tip from the socket followed by pivotal movement of the tip upwardly to disengage the hook means on the stand from the lip on the sheath.

8 Claims, 1 Drawing Sheet

MEDICAL NEEDLE SHEATH AND STAND FOR ONE-HANDED USE

BACKGROUND OF THE INVENTION

1. Field of the Invention

The present invention relates to medical needles and means for safely handling same, and more particularly to a needle sheath and stand or holder therefor which enable one-handed use and disposal of medical needles such as hypodermic needles and electrosurgical probes or so-called needle electrodes.

2. Description of the Prior Art

Because of risk of infection it has become standard practice in medical and health care circles to dispose of medical needles such as hypodermic needles and needle electrodes after one use. As articles of commerce, such needles are supplied to user personnel in sheaths or like containers from which they are withdrawn for use, then returned to after use for disposal. Handling of the needle after the needle has been in contact with a patient exposes the medical user to possible infection with a communicable disease such as AIDS producing virus and there is serious risk of the user inadvertently handling a used needle in such a manner as to accidentally prick a finger or other body part when reinserting a used needle into its sheath for disposal. To avoid such needless risk as much as possible, there have evolved a considerable variety of apparatus and techniques for handling used needles one-handedly, such as providing needle sheaths with flared openings and providing sheath supporting stands or holders for the sheaths.

Various known holders or stands for disposable needles and needle sheaths, for the general purpose of enabling single-handed or one-handed use of a disposable needle are disclosed in Cooke U.S. Pat. No. 5,279,578 (wherein a needle sheath is provided a generally elliptical cross section and is wedged into a notched stand by slight rotation of the sheath), in Halbach U.S. Pat. No. 5,160,324 and Aichimayr U.S. Pat. No. 4,981,476 (in which the needle sheath is retained in a holder by a cocked wedging or cocked wedging and gripping action), in villaveces U.S. Pat. No. 4,921,199, Baskus U.S. Pat. No. 5,102,083, and Capaccio U.S. Pat. No. 5,183,469 (in which threads are provided between a needle sheath and its holder to retain the sheath in the holder), and in Armstrong U.S. Pat. No. 5,334,173 (in which the needle sheath is simply retained on a support surface by means of an adhesive pad).

Another known arrangement for holding a disposable needle sheath in a stand or holder by a gripping action is disclosed in Collett U.S. Pat. No. 5,279,577. In this arrangement, the needle cap holder comprises a base 22 with an indentation 24 in which the tip 20 of the needle sheath 18 fits and above which there is a plate 26 with a V-shaped opening 36 against the sides of which the sheath 18 is pressed to hold the sheath 18 while the needle 16 is withdrawn. Similar holder arrangements are also shown in this patent at FIGS. 3, 6, 7, 8 and 9, all of which have a tip receiving portion such as at 46 in FIG. 3 and a V-shaped opening such as at 48 in FIG. 3 to perform a like sheath gripping function.

SUMMARY OF THE INVENTION

Known sheath holders such as shown in Cooke U.S. Pat. No. 5,279,578 and Collett U.S. Pat. No. 5,279,577 are generally effective in terms of enabling one-handed removal and reinsertion of a disposable needle in its sheath with engagement and disengagement of the sheath with respect to the holder by a simple wedging and unwedging action. However, there is need for a method and apparatus for the purpose of one-handed manipulation of disposable sheathed needles for a more positive retention of the sheath in a stand or holder, without making more complex or complicated the manipulation of the sheath relative to the stand or holder to disengage the sheath from the stand or holder for disposal.

It is accordingly an object and purpose of the present invention to provide a needle sheath and stand combination wherein the needle sheath is positively retained in place on the stand by a hooking arrangement with the sheath thereby being positively retained on the stand and with the sheath nonetheless being readily manipulatable relative to the stand for ease of withdrawal of the sheath from the stand.

It is a further object and purpose of the present invention to provide a needle sheath and stand which are readily fabricated by plastic molding procedures, are economical, and are readily reproduceable on a consistent basis.

These and other objects, features and purposes of the present invention will occur to those skilled in the art to which the invention is addressed, giving due consideration to the accompanying drawings and the following description of typical embodiments thereof.

DESCRIPTION OF THE PREFERRED EMBODIMENTS

Figure 1:
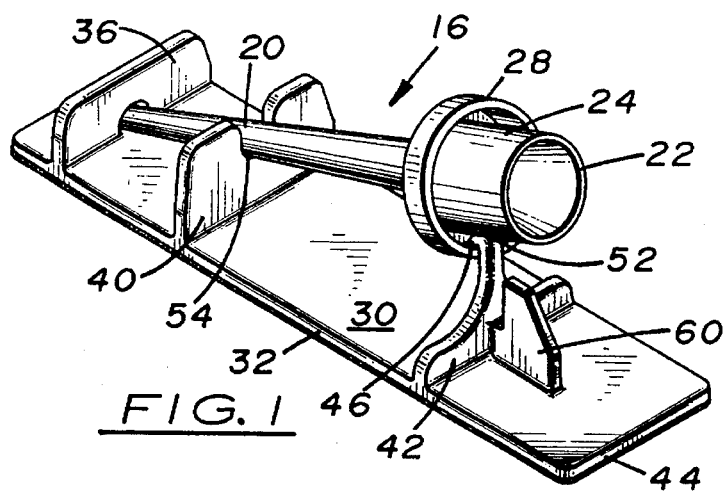
FIG. 1 is a perspective view of a needle electrode sheath and stand, showing the sheath in retained position on the stand.
Figure 2:
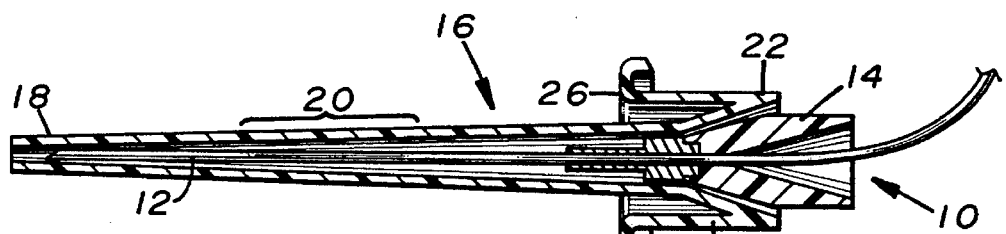
FIG. 2 is a longitudinal cross-sectional view on an enlarged scale of the needle sheath shown in FIG. 1, with a needle electrode installed in the sheath.

FIGS. 1–5 illustrate the presently preferred embodiment of the invention which utilizes in conjunction with a medical needle generally indicated at 10 (FIG. 2) in the form of a monopolar needle electrode, conventional per se, which comprises a needle conductor 12 and a proximal hub 14 which is graspable by a health care user to manipulate the needle. As an article of commerce, such a needle 10 is installed in a sheath, generally indicated at 16. The sheath 16 is of elongate form to house all but the hub portion of the medical needle 10 and comprises a closed, distal end or tip 18, a central portion 20, and a proximal end 22 including a hub portion 24 and a concentric collar 26 including a proximally facing lip 28.

Figure 3:
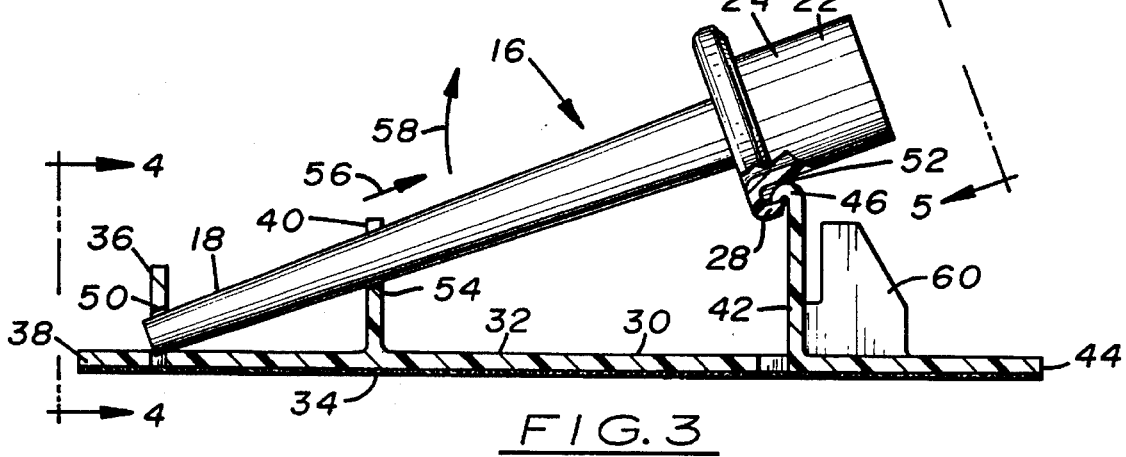
FIG. 3 is a side elevational view, partly in cross section of the sheath and stand shown in FIG. 1, also on an enlarged scale, further showing the constructional detail and interrelation of the sheath and stand components.
Figure 4:
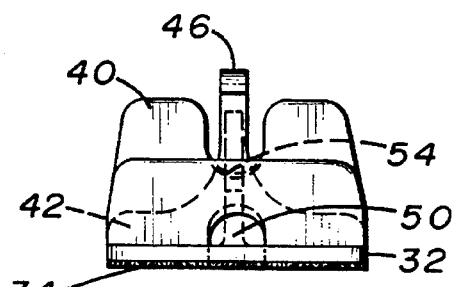
FIG. 4 is an end elevational view of the stand shown in FIGS. 1 and 3, taken substantially along line 4—4 of FIG. 3.
Figure 5:
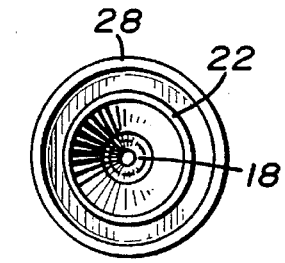
FIG. 5 is an end elevational view of the needle sheath shown in FIGS. 1–3, taken substantially along line 5—5 of FIG. 3.

Used in conjunction with the sheath 16 is a sheath receiving stand generally indicated at 30, also termable a sheath holder, which comprises a generally flat base 32 which is attachable to a supporting surface (not shown) such as a health care user's work station by suitable means such as a contact adhesive layer 34 (FIGS. 3 and 4). In the form illustrated, the stand or holder 30 comprises a first upright member 36 in the form of a laterally extending panel near the distal end 38 of the base 32. A second upright member 40 in the form of a laterally extending panel on the base 32 is situated generally centrally of the base 32. A third upright member 42 in the form of a laterally extending panel is situated near the proximal end 44 of the base 32 and is configured in its upper central portion in the form of a distally facing hook means 46.

A primary feature of the needle sheath and stand arrangement shown as characteristic of the invention is that the sheath 16, when lodged in retained position as shown in FIGS. 1 and 3, is firmly held in essentially fixed position so that it is not likely to move relative to the stand 30 while the needle 10 is being withdrawn and reinserted in the sheath 16. This firm restraint against unintentional movement of the sheath 16 results from the stand 30 having component parts restricting movement at both ends of the sheath 16. One such part is aperture 50 in the upright member 36 near the distal end 38 of the stand base 32 (which aperture is also termable simply a hole or socket) which fixes the position of the distal end or tip 18 of the sheath 16. The other such part, by which the proximal end 22 of the sheath 16 is retained in fixed position, is the hook means 46 on upright member 42 when in engagement with lip 28 on collar 26 of the sheath 16. Upright member 42 positively supports the proximal end 22 of sheath 16 by reason of the contact of the hook means 46 with the hub portion 24 of sheath 16 at the contact point designated 52 in FIG. 3. As shown in FIG. 3, the hook means 46 engages both the hub 24 and the lip 28 of the collar 26, which inhibits any tendency for the sheath to rotate about its longitudinal axis when mounted on the stand. While not essential to the retention of the sheath 16 on the stand or holder 30, the positioning of the sheath 16 on the stand is preferably aided by the configuration of the notch 54 in the upright member 40, since the sides of such notch 54 (note FIGS. 1 and 4) along with the aperture 50 function to guide a sheath 16 placed distal end first into the aperture 50 to the point locking engagement of the hook means 46 with the collar lip 28. In somewhat modified forms, the upright member 40 can be configured to be level along its top at the level of the bottom of the notch 54, if desired, or the member 40 can be dispensed with completely.

As earlier indicated, the stand 30 can be suitably formed of plastic, and at least the portion thereof comprising that part of the upright member 42 in which the hook means 46 is formed is of a resilient nature. Its resiliency not only permits ready engagement of the hook means 46 with the lip 28 when the sheath 16 is placed distal end first on the stand 30, but also to facilitate positive yet controlled removal of the sheath 16 from the stand 30 after reinsertion of a used needle 10 in the sheath 16. Withdrawal of the sheath 16 from the stand 30 is by axial movement of the sheath 16 to the extent of withdrawal of the distal end 18 from the aperture 50, during which axial movement the hook means 46, by reason of its resilient nature, moves proximately with the sheath collar lip 28. Such axial movement of the sheath 16 relative to the stand 30 is schematically indicated in FIG. 3 by the arrow designated 56. Then, once the distal end 18 of the sheath 16 clears the aperture 50 and upright member 36, it is moved pivotally upwardly, as schematically designated by the arrow 58, by what is in effect a rocking movement about a pivot point substantially at the point of contact 52 between the hook means 46 and the sheath hub 24, to a position where the lip 28 of the collar 26 becomes disengaged from the hook means 46, whereupon the sheath and its contained, resheathed, used medical needle can be moved to a location remote from the stand 30 for disposal.

The resilient nature of the upper portion of upright member 42 and its hook means 46, and the repetitive flexing thereof during repeated use of the stand 30, makes it desirable to restrict the extent of movement of hook means 46. This is accomplished by a brace member 60 (FIGS. 1 and 3) which is an upright panel which is integral with the base 32 and the lower portion of upright member 42 but spaced from the upper portion of upright member 42 to enable the desired flexure of the hook means 46.

Substantively, from the point of view of the unique method of one-handedly unsheathing and resheathing a medical electrode with respect to its sheath, the method of use of the sheath and stand of the invention is essentially as follows. With the medical needle installed in the sheath, the tip (18) of the sheath is inserted in a socket (aperture 50) adjacent the distal end (38) of the sheath receiving stand (30) and the distally facing hook means (42) on the stand is engaged with the proximately facing collar lip (28) near the proximate end (22) of the sheath so as to retain the sheath in fixed position on the stand. The needle can then be withdrawn from the sheath for use, and after use is one-handedly reinserted into the sheath on the stand. The health care user then grasps the proximate end of the sheath and withdraws the sheath tip from the socket in the stand a limited extent so that the tip of the sheath clears the socket. With the tip of the sheath disengaged from the socket, the tip is pivotally moved upwardly about an arc of movement (58) centered substantially at the point of contact (52) of the sheath collar lip with the hook means on the stand. Such pivotal movement is continued until the collar lip clears and is disengaged from the hook means. The sheath is then completely withdrawn from the stand by further upward movement while the user continues to one-handedly grasp the sheath at its proximate end and moves the sheath and the used medical needle to a location remote from the stand for disposal or sterilization if the needle is to be reused.

From the foregoing, various further features, adaptations and modifications of the components and arrangement thereof characteristic of the invention will occur to those skilled in the art to which the invention is addressed within the scope of the following claims.

What is claimed is:

1. In a combination comprising:

(1) a medical needle of a type to be disposed after a single use;

(2) an elongate sheath for said needle in which the needle is retained before and after use, said sheath having a distal end and an open, proximal end through which the needle is removable for use and insertable after use, said needle also having a hub portion extending slightly beyond the extent of the sheath when the needle is seated in the sheath so as to be readily graspable by the user for withdrawal of the needle from the sheath and reinsertion of the needle into the sheath; and (3) a sheath receiving stand attachable at a fixed location at a user's work station and in which the sheath is installable and removable in the course of use of the needle by the user;

the improvement wherein said stand comprises a generally flat base, an aperture on said base near the distal end thereof into which the distal end of said sheath can snugly seat; and an upright member on said base near the proximal end thereof with a distally facing hook means located in the upper central portion of said upright panel, said sheath near the proximal end thereof comprising a generally circularly arranged collar including a proximately facing lip engageable with the said hook means when the proximate end of said sheath is in engagement with and supported by said upright member with the sheath distal end in engagement with said aperture, said hook means in engagement with said collar and said aperture in engagement with said sheath distal end cooperatively acting to positively retain the said sheath in fixed position on said stand.

2. The combination of claim 1, wherein the hook means on said upright member is formed of resilient material to enable withdrawal of said sheath from said stand by axial movement of the sheath to withdraw its distal end from the said aperture while said sheath collar bends said hook means in a proximate direction to disengage said sheath distal end from said aperture and then permit upward pivotal movement of the sheath distal end relative to said base to disengage said collar and said hook means.

3. The combination of claim 2, further comprising a bracing member joined with said upright member and situated in spaced relation to and proximately of said hook means to limit the extent of proximal movement of said hook means during withdrawal of the sheath from the stand.

4. In a combination comprising:

(1) a medical needle of a type to be disposed after a single use;

(2) an elongate sheath for said needle in which the needle is retained before and after use, said sheath having a distal end, a central portion, and an open, proximal end through which the needle is removable for use and insertable after use, said needle also having a hub portion extending slightly beyond the extent of the sheath when the needle is seated in the sheath so as to be readily graspable by the user for withdrawal of the needle from the sheath and reinsertion of the needle into the sheath; and (3) a sheath receiving stand attachable at a fixed location at a user's work station and in which the sheath is installable and removable in the course of use of the needle by the user;

the improvement wherein said stand comprises a generally flat base attachable to a supporting surface;

a first upright panel on said base near the distal end thereof, said first upright panel having an aperture situated centrally and at the bottom thereof into which the distal end of said sheath can snugly seat;

a second upright panel on said base comprising a sheath supporting surface in the upper central portion thereof on which the central portion of said sheath is engageable when the distal end of said sheath is in said first upright panel aperture; and a third upright panel on said base near the proximal end thereof with a distally facing hook means located in the upper central portion of said third upright panel, said sheath near the proximal end thereof comprising a generally circularly arranged collar including a proximately facing lip engageable with the said hook means on the said third upright panel when the sheath distal end and sheath central portion are in respective engagement with said first upright panel aperture and said supporting surface of said second upright panel, to positively retain the said sheath in fixed position on said stand.

5. The combination of claim 4, wherein the hook means of the third upright panel is formed of resilient material to enable withdrawal of said sheath from said stand by axial movement of the sheath to withdraw its tip from the said first upright panel aperture while said sheath collar bends said hook means in a proximate direction to disengage said sheath from said aperture and said support surface on said second upright panel by pivotal movement of the distal end of said sheath relative to said base and then upward movement of the said sheath collar to disengage said collar and said hook means.

6. The combination of claim 4, wherein said supporting surface on said second upright panel is in the form of a notch into which said sheath lodges when its distal end in engagement with said aperture and its collar is in engagement with said hook means.

7. The combination of claim 5, wherein said supporting surface on said second upright panel is in the form of a notch into which said sheath fits when its distal end in engagement with said aperture and its collar is in engagement with said hook means.

8. The method of one-handedly unsheathing and resheathing a medical electrode with respect to a medical electrode-covering sheath, said sheath having a distal end and a proximal open end into which the medical needle is insertable and removable, said method of unsheathing and resheathing comprising:

(a) with the medical needle installed in the sheath, inserting the tip of the sheath into a socket adjacent the distal end of the base of a sheath receiving stand and engaging a distally facing hook means on the stand with a proximately facing collar means near the proximate end of the sheath so as to retain the sheath in fixed position on the stand;

(b) withdrawing the medical needle from the sheath for use;

(c) after use of the medical needle, one-handedly reinserting it into the sheath on the stand;

(d) grasping the proximate end of the sheath and withdrawing the sheath tip from the socket in the stand axially a limited extent of movement just sufficient to disengage the tip of the sheath from said socket.

(e) with the distal end of the sheath disengaged from said socket, pivotally moving the tip of the sheath upwardly about an arc of movement centered substantially at the point of contact of the sheath collar means with the hook means on the stand while continuing such pivotal movement until said collar means clears and is disengaged from said hook means;

(f) completely withdrawing the sheath from the stand by further upward movement while continuing to one-handedly grasp the sheath at its proximate end; and (g) moving the sheath and its resheathed, used medical needle to a location remote from the stand.

* * * * *